(12) United States Patent
Hong et al.

(10) Patent No.: US 6,974,472 B2
(45) Date of Patent: Dec. 13, 2005

(54) FLEXIBLE SELF-EXPANDABLE STENT USING SHAPE MEMORY ALLOY AND METHOD AND APPARATUS FOR FABRICATING THE SAME

(75) Inventors: Soon-Hyung Hong, Taejeon (KR); Woong-Hee Son, Choong Cheongbuk-Do (KR); Jae-Hyung Park, Seoul (KR); Jong-Taek Lee, Seoul (JP); Jin-Wook Jung, Seoul (KR); Kyoung-Min Shin, Seoul (KR)

(73) Assignee: Taewoong Medical Co., Ltd., Seoul (KR)

( * ) Notice: Subject to any disclaimer, the term of this patent is extended or adjusted under 35 U.S.C. 154(b) by 511 days.

(21) Appl. No.: 10/098,431

(22) Filed: Mar. 18, 2002

(65) Prior Publication Data

US 2002/0147489 A1 Oct. 10, 2002

(30) Foreign Application Priority Data

Apr. 4, 2001 (KR) ......................................... 2001-18025

(51) Int. Cl.$^7$ .................................................. A61F 2/06
(52) U.S. Cl. ...................... 623/1.15; 623/1.18; 623/901
(58) Field of Search ............................. 623/1.13, 1.15, 623/1.18–1.2

(56) References Cited

U.S. PATENT DOCUMENTS 5,545,211 A * 8/1996 An et al. ..................... 623/1.2
6,187,036 B1 * 2/2001 Shaolian et al. ........... 623/1.15
6,312,458 B1 * 11/2001 Golds ......................... 623/1.13

* cited by examiner

Primary Examiner—Julian W. Woo
Assistant Examiner—Sarah Webb
(74) Attorney, Agent, or Firm—Jagtiani +Guttag

(57) ABSTRACT

Disclosed herein is a flexible self-expandable stent using shape memory alloy for expanding stenosal portions and method and apparatus for fabricating the same. The self-expandable stent using shape memory allow, comprises a first cylindrical stent member comprised of a first wire formed of super elastic shape memory alloy, the first wire being bent a large number of times while being extended upwardly and downwardly a large number of times, so the first wire forms a plurality of variable rhombic spaces by forming a plurality of intersections for causing the first wire to be intersected with itself to resist longitudinal constriction of the first cylindrical stent member and a plurality of interlocked points for causing the first wire to be interlocked with itself at spaced positions to allow longitudinal constriction of the first cylindrical stent member; and a second cylindrical stent member comprised of a second wire formed of super elastic shape memory alloy, the second wire being diagonally extended in parallel with the previously positioned first wire and passed alternately under and over the first wire so as to divide each of a plurality of rhombic spaces formed in the first cylindrical stent member into four equal parts, thereby preventing the first and second cylindrical stent members from being separated from each other.

1 Claim, 13 Drawing Sheets

FLEXIBLE SELF-EXPANDABLE STENT USING SHAPE MEMORY ALLOY AND METHOD AND APPARATUS FOR FABRICATING THE SAME

BACKGROUND OF THE INVENTION

1. Field of the Invention

The present invention relates generally to a flexible self-expandable stent using shape memory alloy for expanding stenosal portions and method and apparatus for fabricating the same, and more particularly to a flexible self-expandable stent using shape memory alloy and method and apparatus for fabricating the same, used to be situated in and expand the passages of stenosal portions so as to deal with the stenosis of a blood vessel caused by thrombus and the stenosis of the gullet, the gall duct and the urethra caused by cancer tissues and the formation of the artificial passage in the jugular vein, which is capable of being positioned to fit the shape of the passage of the stenosal portion regardless of the shape of the passage, such as a straight (horizontal or vertical) passage and a winding passage, while maintaining its transversal elasticity, thereby maintaining the shape of the passage and minimizing the deformation of the stenosal portion.

2. Description of the Prior Art

In general, a blood vessel is blocked or constricted because of thrombus, arteriosclerosis or the like, so a variety of disorders occur.

When a blood vessel is being constricted or has been constricted, the stenosal portion of the blood vessel is treated through artificial vessel replacement or angioplasty by means of a surgical operation.

However, such a surgical operation requires the incision of the large body region around a pathological portion, so a large scar remains, a long period of convalescence is required and the insufficient effect of an operation is achieved.

In particular, most vascular diseases are caused by hypertension and a heart disease, so it is impossible to treat most vascular disease by means of the surgical operation.

In order to overcome such a problem, there is employed angioplasty without an surgical operation, in which a small hole is bored into a femoral artery, a balloon catheter tube is inserted into a stenosal portion through the small hole from the outside of the body into the inside of a blood vessel, and the balloon of the balloon catheter tube is inflated.

However, in accordance with angioplasty, a blood vessel is re-constricted three or four months after an operation. Accordingly, angioplasty should be carried out again, so there occurs a problem that a patient should undergo pain and economic difficulty.

Excepting such vascular diseases, when the gullet is blocked by cancer tissues, it is impossible to take food through the mouth. Accordingly, a hole is formed from the abdomen to the stomach and foot is supplied to the stomach through a tube, so pain is caused to a patient and his caregivers.

The stenosis of the gall duct and the urethra, the formation of the artificial passage in the jugular vein and the stenosis and blockade of the internal organs are dealt with in such a way.

In such cases, there occurs a problem that mental or economic burden is imposed on a patient and his caregivers.

In order to solve the problems of the prior art, the present inventors filed an expandable stent using shape memory alloy and method for fabricating the expandable stent (Korean Pat. Appln. No. 98-13572). This application, as can be seen in FIGS. 1 to 4, discloses a prior art expandable stent in which a super-elastic shape memory alloy wire 1 is intersected with itself and woven to form a plurality of rhombic spaces 2 and a hollow cylindrical body 3 having a certain length, a plurality of entrance and exit bends are formed at both ends of the hollow cylindrical body 3, and both ends 6 and 7 of the super-elastic shape memory alloy wire 1 are welded together. In the placement of the expandable stent, the hollow cylindrical body 3 is considerably reduced in volume by compressing the rhombic spaces 2 and the prior art expandable stent 8 is pushed into a pathological portion B-1 within a vessel B using a guide catheter G.T and a pusher catheter P.C, thereby expanding the vessel B by pushing the pathological portion B-1 radially outwardly. Accordingly, the prior art expandable stent 8 can be semi-permanently utilized to expand the stenosal portion of the body.

The use of the prior art technology of the present inventors is described with reference to FIG. 3. The position, length and inner diameter of the pathological portion B-1 situated within the vessel B are examined by means of a fluoroscope used in angioplasty, and the required portion is firstly anesthetized.

In this state, the guide tube G.T is inserted into the vessel B to reach the pathological portion B-1, and the prior art expandable stent 8 is inserted into the guide tube G.T while being constricted in width (diameter). In this state, the prior art expandable stent 8 is pushed into the pathological portion B-1 using a pusher catheter P.C.

The expandable stent 8 positioned in the pathological portion B-1 is restored to its original shape while being removed from the guide tube G.T, and simultaneously pushes the pathological portion situated in the vessel B to expand the vessel B, thereby expanding the passage of the vessel B of the stenosal portion.

In this case, the prior art expandable stent 8, as shown in FIG. 1, has the diameter Ø 10 to 30% larger than that of an applied portion, that is, a portion of a blood vessel B, and the length L longer than that of an applied portion, that is, a portion of a blood vessel B.

In accordance with the previously filed prior art of the present inventors, the expandable stent using super-elastic shape memory alloy wire 1 and having a diameter Ø and a length L has radial and longitudinal elasticity tending to be restored to its original state unless the shape memory alloy wire 1 is forcibly compressed by external force.

However, the expandable stent 8 in accordance with the prior art can be applied to the straight line-shaped vessel B without hindrance, but is not applicable to a winding stenosal vessel B shown in FIG. 4, thereby decreasing the usability of the expandable stent 8.

The reason for this is that when the prior art expandable stent 8 is inserted into the winding stenosal vessel B, the prior art expandable stent 8 does not maintain the shape corresponding to that of the winding vessel B but is restored to its straight line (horizontal or vertical) shape. Accordingly, the vessel B is lengthened and the winding portion of the vessel B is straightened (horizontally or vertically, so the entrance of the vessel B is deformed to be narrower than its original size (t→t−a), thereby hindering the circulation of material and deteriorating the function of the expandable stent.

SUMMARY OF THE INVENTION

Accordingly, the present invention has been made keeping in mind the above problems occurring in the prior art, and an object of the present invention is to provide a self-expandable stent used to be situated in and expand the passage of a stenosal portion, which is capable of being positioned to fit the shape of the passage of the stenosal portion regardless of the shape of the passage, such as a straight (horizontal or vertical) passage and a winding passage, while maintaining its transversal elasticity, thereby maintaining the original shape of the passage and minimizing the deformation of the stenosal portion.

In order to accomplish the above object, the present invention provides a self-expandable stent using shape memory allow, comprising: a first cylindrical stent member comprised of a first wire formed of super elastic shape memory alloy, the first wire being bent a large number of times while being extended upwardly and downwardly a large number of times, so the first wire forms a plurality of variable rhombic spaces by forming a plurality of intersections for causing the first wire to be intersected with itself to resist longitudinal constriction of the first cylindrical stent member and a plurality of interlocked points for causing the first wire to be interlocked with itself at spaced positions to allow longitudinal constriction of the first cylindrical stent member; and a second cylindrical stent member comprised of a second wire formed of super elastic shape memory alloy, the second wire being diagonally extended in parallel with the previously positioned first wire and passed alternately under and over the first wire so as to divide each of a plurality of rhombic spaces formed in the first cylindrical stent member into four equal parts, thereby preventing the first and second cylindrical stent members from being separated from each other.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
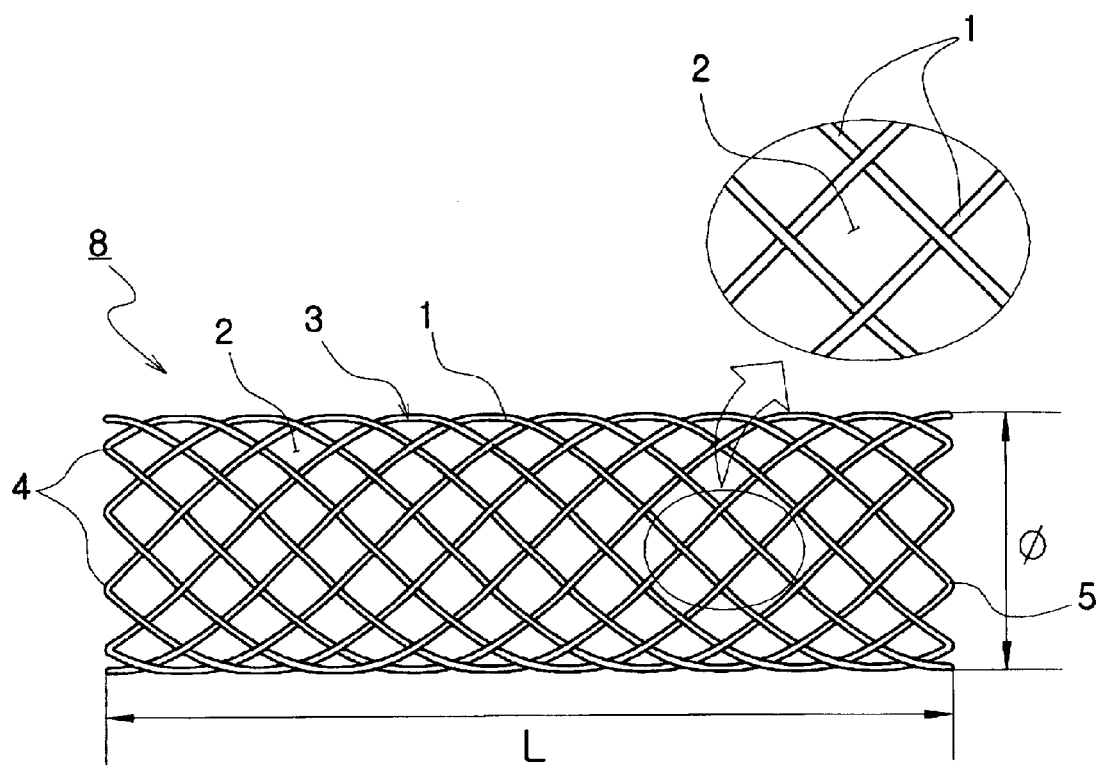
FIG. 1 is a front view of a prior art expandable stent.
Figure 2:
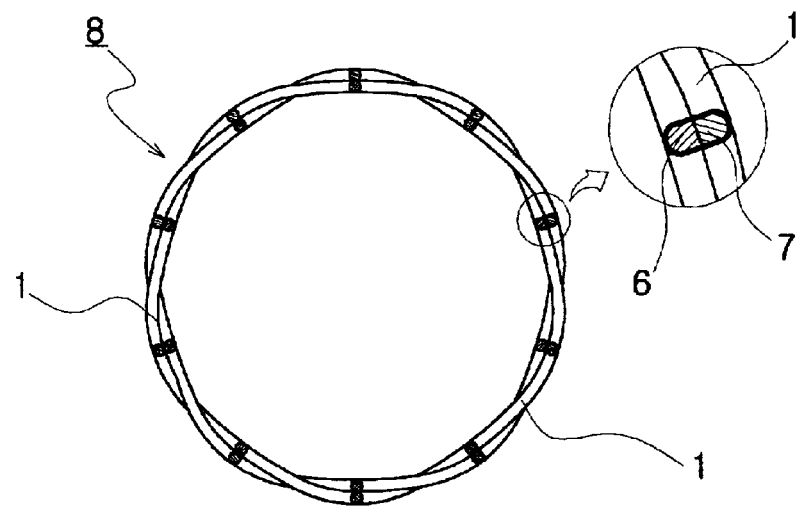
FIG. 2 is a side sectional view of FIG. 1.
Figure 3:
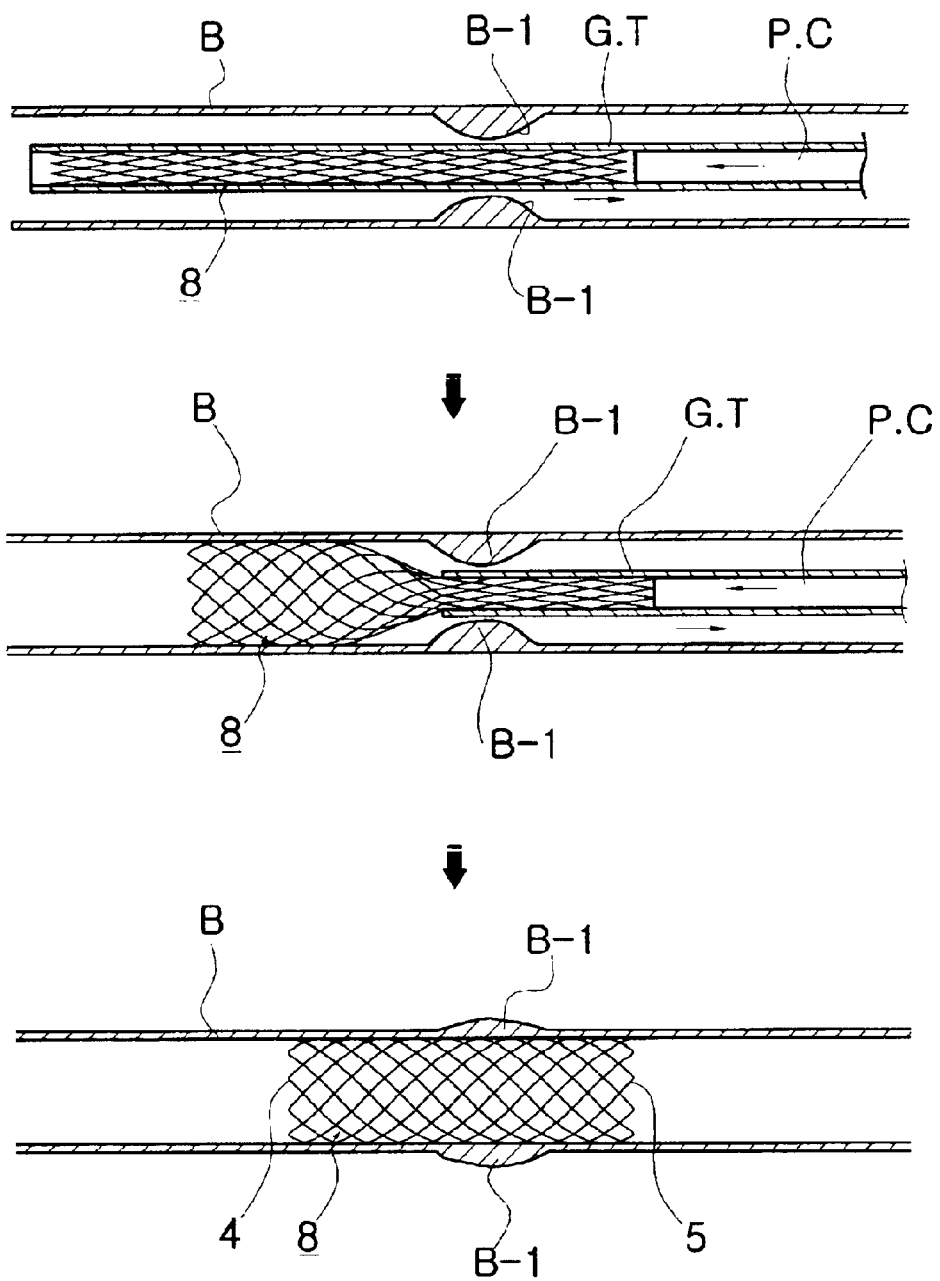
FIG. 3 is a view showing the operation of the prior art expandable stent of FIG. 1.
Figure 4:
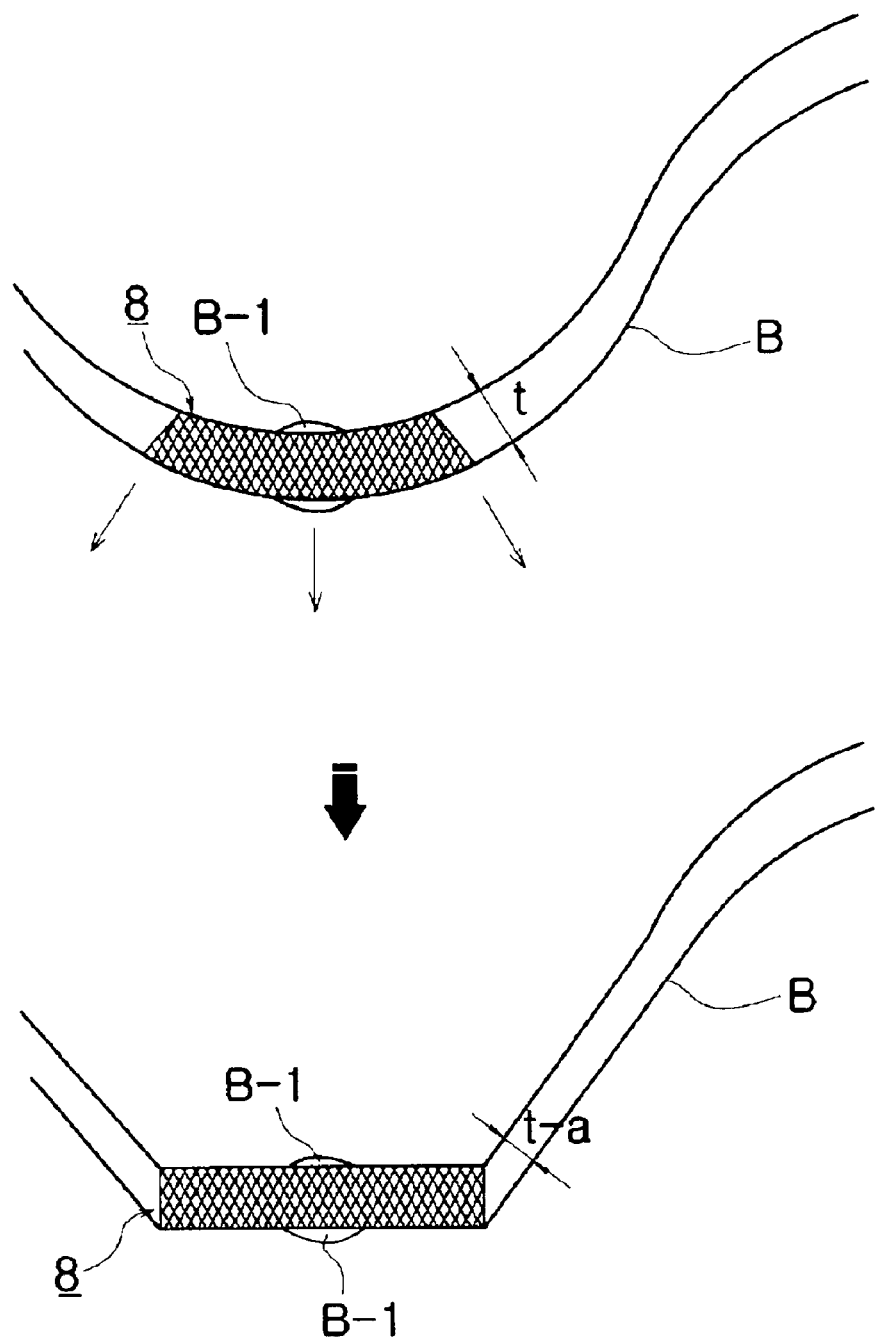
FIG. 4 is a view showing the application of the prior art expandable stent of FIG. 1 to a blood vessel.

Hereinafter, the present invention is described in detail with reference to FIGS. 5 to 13.

The material of a wire employed in the present invention is the same as that of the invention of a patent application previously filed by the inventors of the present invention.

The material employed in the present invention is shape memory alloy that can be formed in the shape of a hollow cylinder and heat-treated to be restored to its original shape at a predetermined temperature.

There are utilized various kinds of shape memory alloy. Ni—Ti line alloy, which has super-elasticity after heat treatment and superior shape memory characteristics, is most suitable for the embodying of the present invention.

The self-expandable stent of the present invention is fabricated using two super-elastic shape memory alloy wires each having a diameter ranging from 0.1 to 0.5 mm. A first cylindrical stent member X is comprised of a first wire 10 formed of super-elastic shape memory alloy. The first wire 10 is bent a large number of times while being extended upwardly and downwardly a large number of times, so the first wire 10 forms a plurality of variable rhombic spaces 20 by forming a plurality of intersections 70 for causing the first wire 10 to be intersected with itself to resist the longitudinal constriction of the first cylindrical stent member X and a plurality of interlocked points 60 for causing the first wire 10 to be interlocked with itself at spaced positions to allow the longitudinal constriction of the first cylindrical stent member X. A second cylindrical stent member Y is comprised of a second wire 11. The second wire 11 is diagonally extended in parallel with the previously positioned first wire 10 and passed alternately under and over the first wire 10 so as to divide each of a plurality of rhombic spaces formed in the first cylindrical stent member X into four equal parts. The self-expandable stent 80 of the present invention is completed by joining together the first and second cylindrical stent member members X and Y.

Figure 5:
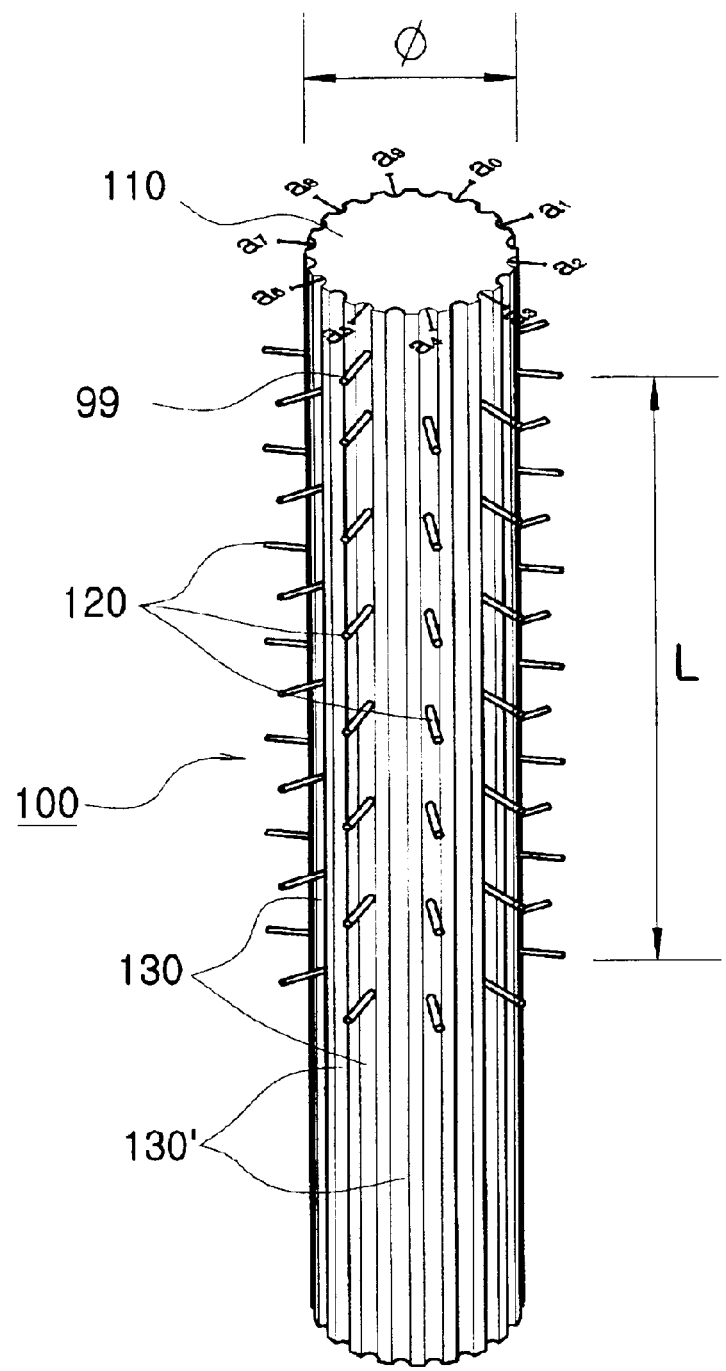
FIGS. 5 and 6 are a perspective view and a sectional view showing the base jig of the present invention, respectively.
Figure 6:
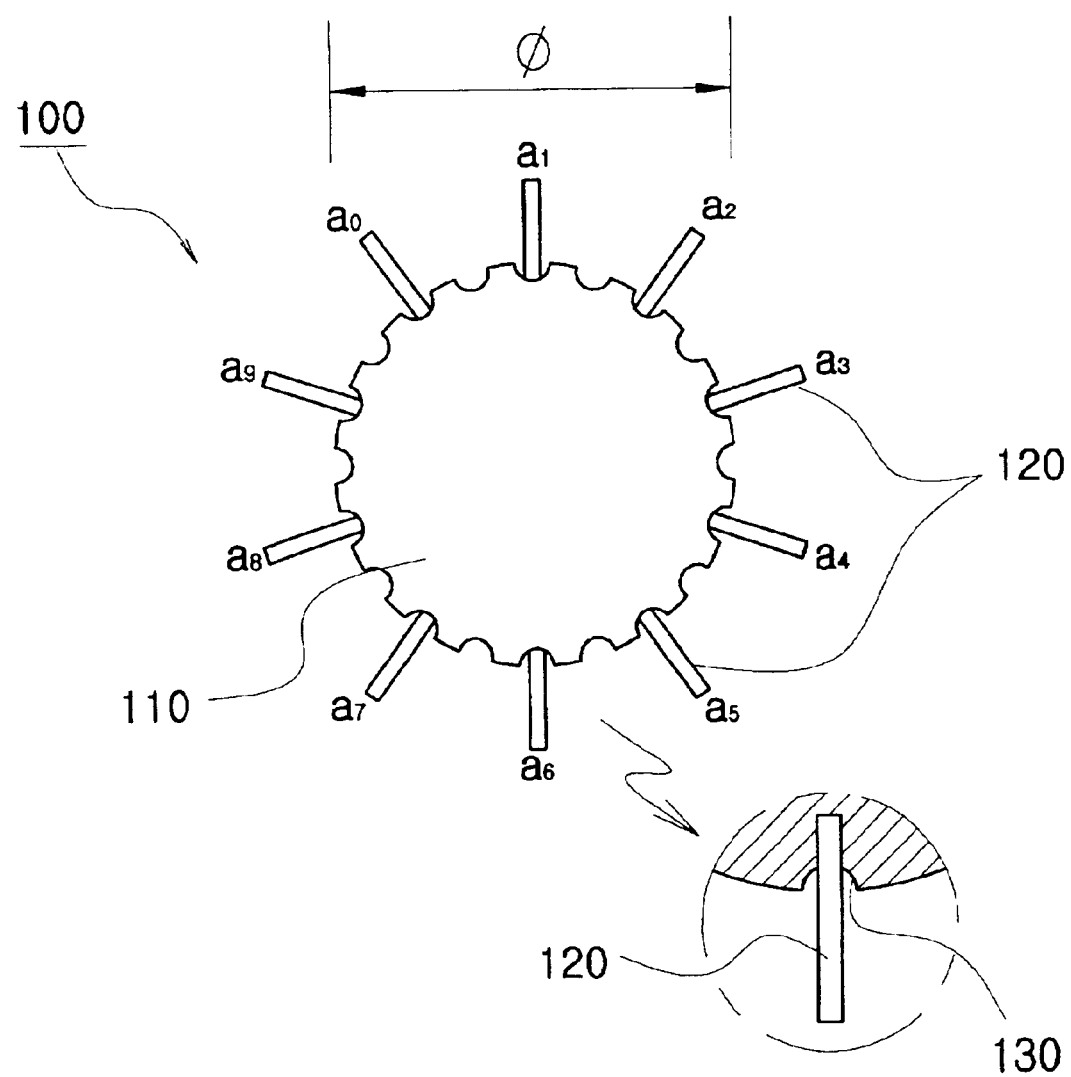

FIGS. 5 and 6 are views illustrating a stent fabricating apparatus. A cylinder 110 having a desired diameter Ø and a desirable length L is utilized to fabricate the self-expandable stent 80 of the present invention. In this case, a plurality of circumference dividing lines a0, a1, a2, a3, - - -, a9 and a plurality of length dividing lines b0, b1, b2, b3, - - -, b7 are set by regularly dividing the circumference W and length L of the cylinder 110, respectively.

A plurality of assembly grooves 130 are formed along the length of the cylinder 110 with reference to the circumference dividing lines a0, a1, a2, a3, - - -, a9. A plurality of projected pins 120 are detachably implanted at all the intersections between the circumference dividing lines a0, a1, a2, a3, - - -, a9 and the length dividing lines b0, b1, b2, b3, - - -, b7 at their one-side ends. A plurality of assembly auxiliary grooves 130' are each formed between two neighboring assembly grooves 130.

The above-described setting is for the understanding of the present invention.

In other words, although the present invention is described using the circumference dividing lines a0, a1, a2, a3, - - -, a9 and the length dividing lines b0, b1, b2, b3, b7 set by regularly dividing the circumference W and length L of the cylinder 110 of the base jig 100, this is for easy understanding of the present invention. Accordingly, the circumference dividing lines and the length dividing lines can be optionally set according to the size of the stent 80, that is, the diameter and length of the stent 80.

In other words, a plurality of assembly grooves 130 are formed with reference to a relatively large or small number of circumference dividing lines a0, a1, a2, a3, - - -, a9, - - - and a relatively large or small number of length dividing lines b0, b1, b2, b3, - - -, b7, - - - can be set as described beforehand, thus fabricating the self-expandable stent 80 of the present invention.

A fixing pin 99 is implanted at the uppermost position of the base jig 100.

FIGS. 7a to 7d are development views showing a developed base jig 100 so as to describe the fabrication method of the present invention.

The procedure for fabricating the first cylindrical stent member X is described with reference to FIGS. 7a and 7b.

Figure 7A:
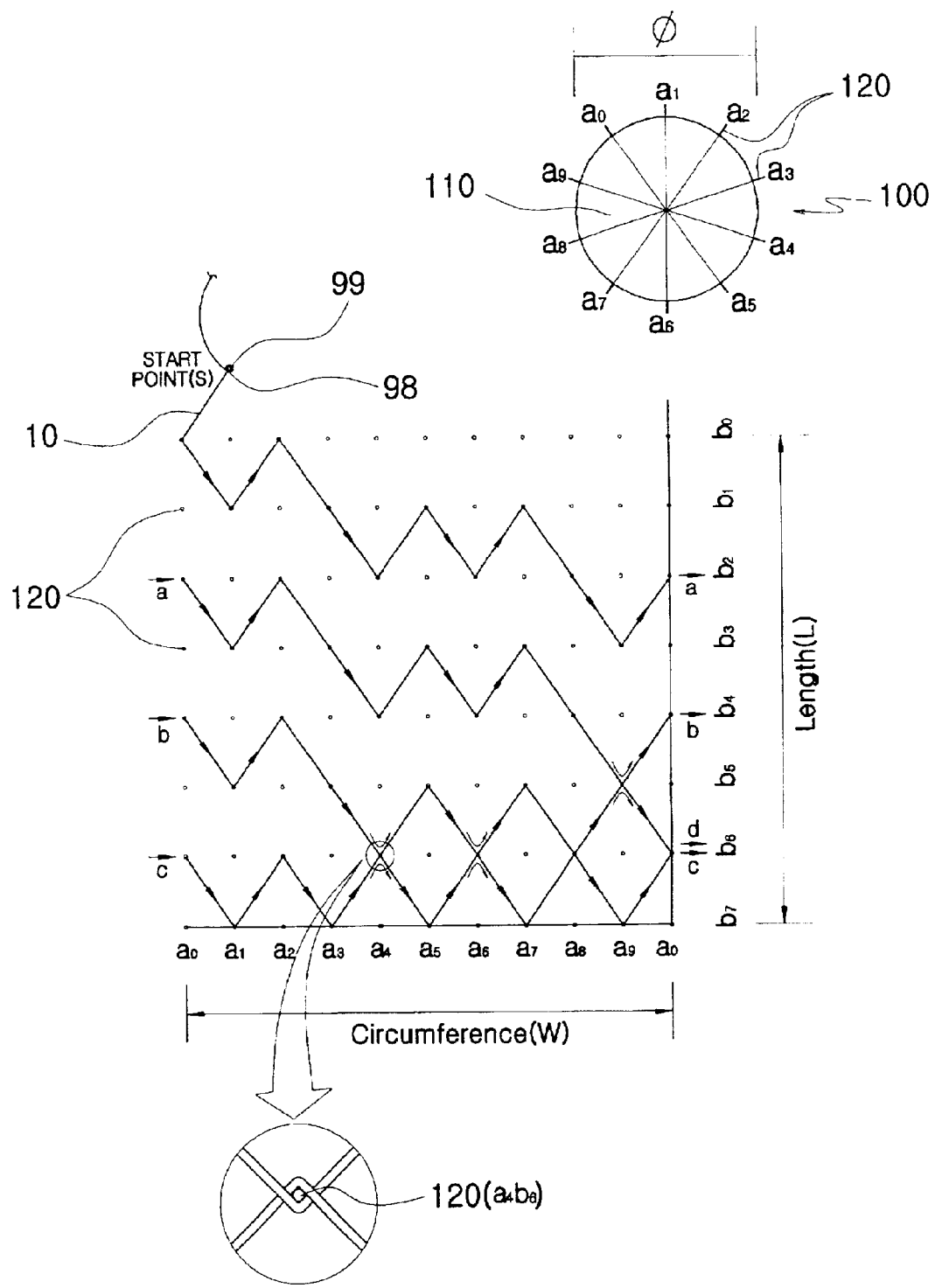
FIGS. 7a, 7b, 7c and 7d are development views showing the fabrication method of the present invention.

As shown in FIG. 7a, a knot 98 is formed by tying a first wire 10 at its one end. The knot 98 is inserted into the pin 99 to secure the wire 10.

The knot 98 is selected as a start point S for convenience.

One of the circumference dividing lines a0, a1, a2, a3, - - -, a9 is selected as a first reference line a0. The first wire 10 is diagonally extended while being diagonally downwardly passed by a projected pin 120 (its position: a0b0) situated at the uppermost position of the first reference line a0, and hooked around a projected pin 120 (its position: a1b1) by passing the first wire 10 under the projected pin 120 (its position: a1b1).

In such a case, the length by which the first wire 10 has been diagonally extended is referred to as a diagonal length for convenience.

After the first wire 10 is hooked around the projected pin 120 (its position: a1b1) by passing the first wire 10 under the projected pin 120 (its position: a1b1) and diagonally upwardly extending it, the first wire 10 undergoes the process in which the first wire 10 is hooked around a projected pin 120 (its position: a2b0) by passing the first wire 10 over the projected pin 120 (its position: a2b0) and diagonally downwardly extending the first wire 10.

Thereafter, the first wire 10 is extended to a projected pin 120 (its position: a4b2) by the diagonal distance of 2, and passed under the projected pin 120 (its position: a4b2) and extended diagonally upwardly.

Thereafter, the first wire 10 is extended to a projected pin 120 (its position: a5b1) by the diagonal distance of 1, and passed over the projected pin 120 (its position: a5b1) and extended diagonally downwardly. Thereafter, the first wire 10 is extended to a projected pin 120 (its position: a6b2) by the diagonal distance of 1, and passed under the projected pin 120 (its position: a6b2) and extended diagonally upwardly.

In such a state, after the first wire 10 is hooked around a projected pin 120 (its position: a7b1) by diagonally upwardly extending the first wire 10 by the diagonal distance of 1 and passing it over the projected pin 120 (its position: a7b3), the first wire 10 is hooked around a projected pin 120 (its position: a9b3) by diagonally downwardly extending the first wire 10 by the diagonal distance of 2 and passing it under the projected pin 120 (its position: a9b3).

After such a process, the first wire 10 is hooked around a projected pin 120 (its position: a0b2) by passing the first wire 10 over the projected pin 120 (its position: a0b2), and, thereafter, is hooked around a projected pin 120 (its position: a1b3) by passing the first wire 10 under the projected pin 120 (its position: a1b3).

As described above, after the first wire 10 has been hooked around the projected pin 120 (its position: a1b3) while diagonally downwardly passing the first wire 10 under the projected pin 120 (its position: a1b3), the first wire 10 is hooked around a projected pin 120 (its position: a2b2) by diagonally upwardly extending the first wire 10 and passing it over the projected pin 120 (its position: a2b2). Thereafter, the first wire 10 is extended to a projected pin 120 (its position: a4b4) by the diagonal distance of 2, and hooked around the projected pin 120 (its position: a4b4) by passing the first wire 10 under the projected pin 120 (its position: a4b4).

After such a process is completed, the first wire 10 is diagonally upwardly extended to a projected pin 120 (its position: a5b3) by the diagonal distance of 1, and hooked around the projected pin 120 (its position: a5b3) by passing the first wire 10 over the projected pin 120 (its position: a5b3).

Next, the first wire 10 is hooked around a projected pin 120 (its position: a6b4) by diagonally upwardly extending the first wire 10 under a projected pin 120 (its position: a6b4) by the diagonal distance of 1 and passing it over the projected pin 120 (its position: a6b4).

In such a state, after the first wire 10 is hooked around a projected pin 120 (its position: a7b3) by diagonally upwardly extending the first wire 10 by the diagonal distance of 1 and passing it over the projected pin 120 (its position: a7b3), the first wire 10 is hooked around a projected pin 120 (its position: a9b5) by diagonally downwardly extending the first wire 10 by the diagonal distance of 2 and passing it under the projected pin 120 (its position: a9b5).

After such a process, the first wire 10 is hooked around a projected pin 120 (its position: a0b4) by passing the first wire 10 over the projected pin 120 (its position: a0b4), and, thereafter, is hooked around a projected pin 120 (its position: a1b5) by passing the first wire 10 under the projected pin 120 (its position: a1b5).

As described above, since the first wire 10 has been hooked around the projected pin 120 (its position: a1b5) while passing the first wire 10 under the projected pin 120 (its position: a1b5), the first wire 10 should be hooked around a projected pin 120 (its position: a2b4) by diagonally upwardly extending the first wire 10 and passing it over the projected pin 120 (its position: a2b4). Thereafter, the first wire 10 is extended to a projected pin 120 (its position: a2b4) by the diagonal distance of 2, and hooked around the projected pin 120 (its position: a4b6) by passing the first wire 10 under the projected pin 120 (its position: a4b6).

After such a process is completed, the first wire 10 is diagonally upwardly extended to a projected pin 120 (its position: a5b5) by the diagonal distance of 1, and hooked around the projected pin 120 (its position: a5b5) by passing the first wire 10 over the projected pin 120 (its position: a5b5).

Next, the first wire 10 is hooked around a projected pin 120 (its position: a6b6) by diagonally upwardly extending the first wire 10 under a projected pin 120 (its position: a6b6) by the diagonal distance of 1 and passing it over the projected pin 120 (its position: a6b6).

In such a state, after the first wire 10 is hooked around a projected pin 120 (its position: a7b5) by diagonally upwardly extending the first wire 10 by the diagonal distance of 1 and passing it over the projected pin 120 (its position: a7b5), the first wire 10 is hooked around a projected pin 120 (its position: a9b7) by diagonally downwardly extending the first wire 10 by the diagonal distance of 2 and passing it under the projected pin 120 (its position: a9b7).

In such a state, after the first wire 10 is hooked around a projected pin 120 (its position: a0b6) by diagonally upwardly extending the first wire 10 by the diagonal distance of 1 and passing it over the projected pin 120 (its position: a0b6), the first wire 10 is hooked around a projected pin 120 (its position: a1b7), a projected pin 120 (its position: a2b7), a projected pin 120 (its position: a3b7) and a projected pin 120 (its position: a4b6).

In this case, the projected pin 120 (its position: a4b6) is used for allowing the first wire 10 to be twice hooked around itself. As shown in the enlarged view of FIG. 7a, the later hooked first wire 10 is hooked around the projected pin 120 in such a way that the later hooked first wire 10 is passed under the previously hooked first wire 10, hooked around the projected pin 120 (its position: a4b6), and passed over the previously hooked first wire 10.

This process can be performed using the assembly auxiliary grooves 130' formed on the base jig 100.

In such a state, the first wire 10 reaches a projected pin 120 (its position: a5b7) and a projected pin 120 (its position: a6b6). In this case, the first wire 10 is twice hooked around the projected pin 120 (its position: a6b6) in the same way as that for the projected pin 120 (its position: a4b6).

In such a state, the first wire 10 reaches a projected pin 120 (its position: a7b7) and a projected pin 120 (its position: a8b6). In this case, the first wire 10 is twice hooked around the projected pin 120 (its position: a8b6) in the same way as that for the projected pin 120 (its position: a4b6).

Thereafter, after the first wire 10 is hooked around a projected pin 120 (its position: a9b7), the first wire 10 is diagonally upwardly extended by the distance of 2 and hooked around a projected pin 120 (its position: a1b5).

Figure 7B:
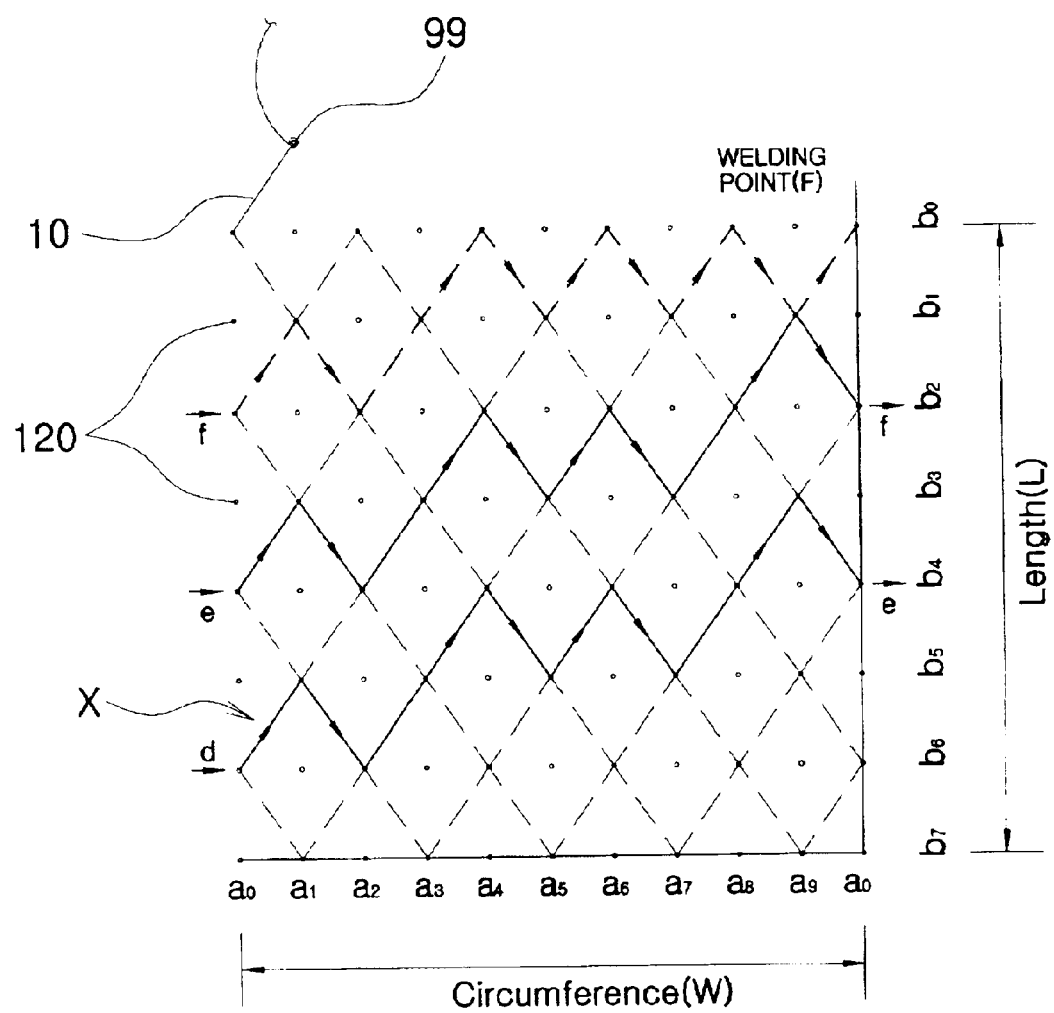

Such a process is indicated as the arrow "d" of FIG. 7a and the arrow "d" of FIG. 7b associated with each other. The arrows "a", "b" and "c" of FIG. 7a are marks for indicating the extending paths of the first wire 10 so as to allow the present invention to be easily understood.

The dotted lines of FIG. 7b indicate the first wire 10 that has undergone the above-described procedure, while the solid lines of FIG. 7b indicate the first wire 10 that will undergo the below-described procedure.

After the first wire 10 is hooked around the projected pin 120 (its position: a1b5) by diagonally downwardly extending the first wire 10 from the projected pin 120 (its position: a1b5) by the diagonal distance of 1 and passing the first wire 10 under the projected pin 120 (its position: a2b6), the first wire 10 is hooked around the projected pin 120 (its position: a4b4) by diagonally upwardly extending the first wire 10 by the diagonal distance of 2 and passing the first wire 10 over the projected pin 120 (its position: a4b4). Thereafter, the first wire 10 is hooked around the projected pin 120 (its position: a6b4) by diagonally upwardly extending the first wire 10 by the diagonal distance of 1 and passing the first wire 10 over the projected pin 120 (its position: a6b4).

After the first wire 10 is hooked around the projected pin 120 (its position: a7b5) by diagonally downwardly extending the first wire 10 by the diagonal distance of 1 and passing the first wire 10 under the projected pin 120 (its position: a7b5), the first wire 10 is hooked around the projected pin 120 (its position: a9b3) by diagonally upwardly extending the first wire 10 by the diagonal distance of 2 and passing the first wire 10 over the projected pin 120 (its position: a9b3). Thereafter, the first wire 10 is hooked around the projected pin 120 (its position: a0b4) by diagonally upwardly extending the first wire 10 by the diagonal distance of 1 and passing the first wire 10 over the projected pin 120 (its position: a5b3) (refer to arrow "e").

After the first wire 10 is hooked around the projected pin 120 (its position: a6b2) by diagonally upwardly extending the first wire 10 by the diagonal distance of 1 and passing the first wire 10 over the projected pin 120 (its position: a6b2), the first wire 10 is hooked around the projected pin 120 (its position: a7b3) by diagonally downwardly extending the first wire 10 by the diagonal distance of 1 and passing the first wire 10 under the projected pin 120 (its position: a7b3).

After the first wire 10 is hooked around the projected pin 120 (its position: a9b1) by diagonally upwardly extending the first wire 10 by the diagonal distance of 2 and passing the first wire 10 over the projected pin 120 (its position: a6b2), the first wire 10 is hooked around the projected pin 120 (its position: a0b2) by diagonally downwardly extending the first wire 10 by the diagonal distance of 1 and passing the first wire 10 under the projected pin 120 (its position: a0b2) (refer to arrow "f").

After the first wire 10 is hooked around the projected pin 120 (its position: a1b1) by diagonally upwardly extending the first wire 10 by the diagonal distance of 1 and passing the first wire 10 under the projected pin 120 (its position: a1b1), the first wire 10 is hooked around the projected pin 120 (its position: a2b2) by diagonally downwardly extending the first wire 10 by the diagonal distance of 1 and passing the first wire 10 over the projected pin 120 (its position: a2b2). Thereafter, the first wire 10 is hooked around the projected pin 120 (its position: a4b0) by diagonally upwardly extending the first wire 10 by the diagonal distance of 2 and passing the first wire 10 under the projected pin 120 (its position: a4b0).

The first wire 10 is hooked on the projected pins (their positions: a6b0, a7b1, a8b0 and a9b1) by diagonally and downwardly extending the first wire 10 by the diagonal length of 1 and alternately passing the first wire 10 by the projected pins (their positions: a6b0, a7b1, a8b0 and a9b1).

After the first wire 10 is hooked on the projected pin 120 (its position: a9b1), the first wire 10 reaches the initial projected pin (its position: a9b1). There is fabricated the first cylindrical stent member X in which its both ends are connected to each other by welding together both ends of the first wire 10 meeting each other, or inserting both ends of the first wire 10 into a sleeve 200 and pressing them.

As described above, in fabricating the first cylindrical stent member X, the first cylindrical stent member X is fabricated in the process of extending the first wire 10 from the top of the jig 100 to the bottom of the jig 100 and from the bottom of the jig 100 to the top of the jig 100.

In such a case, when the first wire 10 is desired to be hooked around the same projected pin 120 as that around which the first wire 10 has been hooked, the first wire 10 should be passed under or over the previously placed first wire 10 so that the first wire 10 is situated at high and low positions.

Figure 7C:
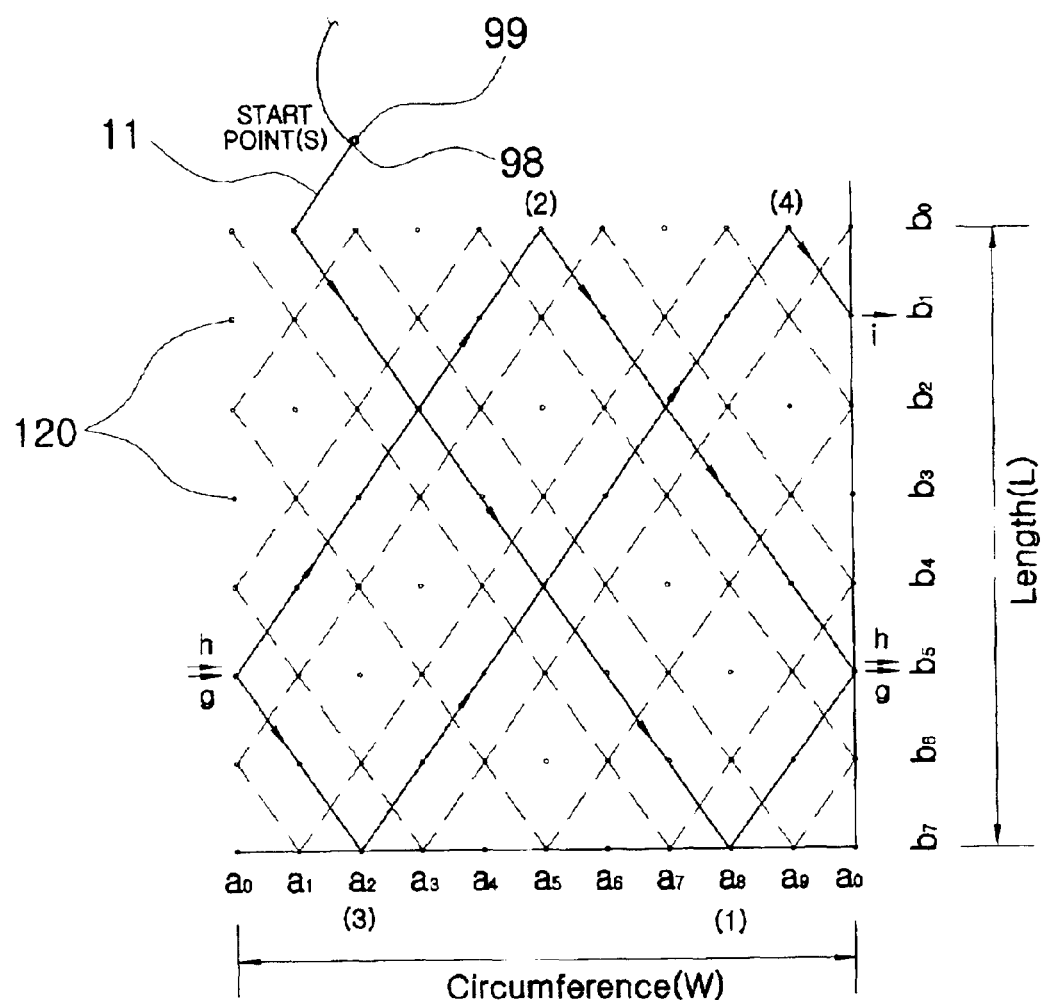
Figure 7D:
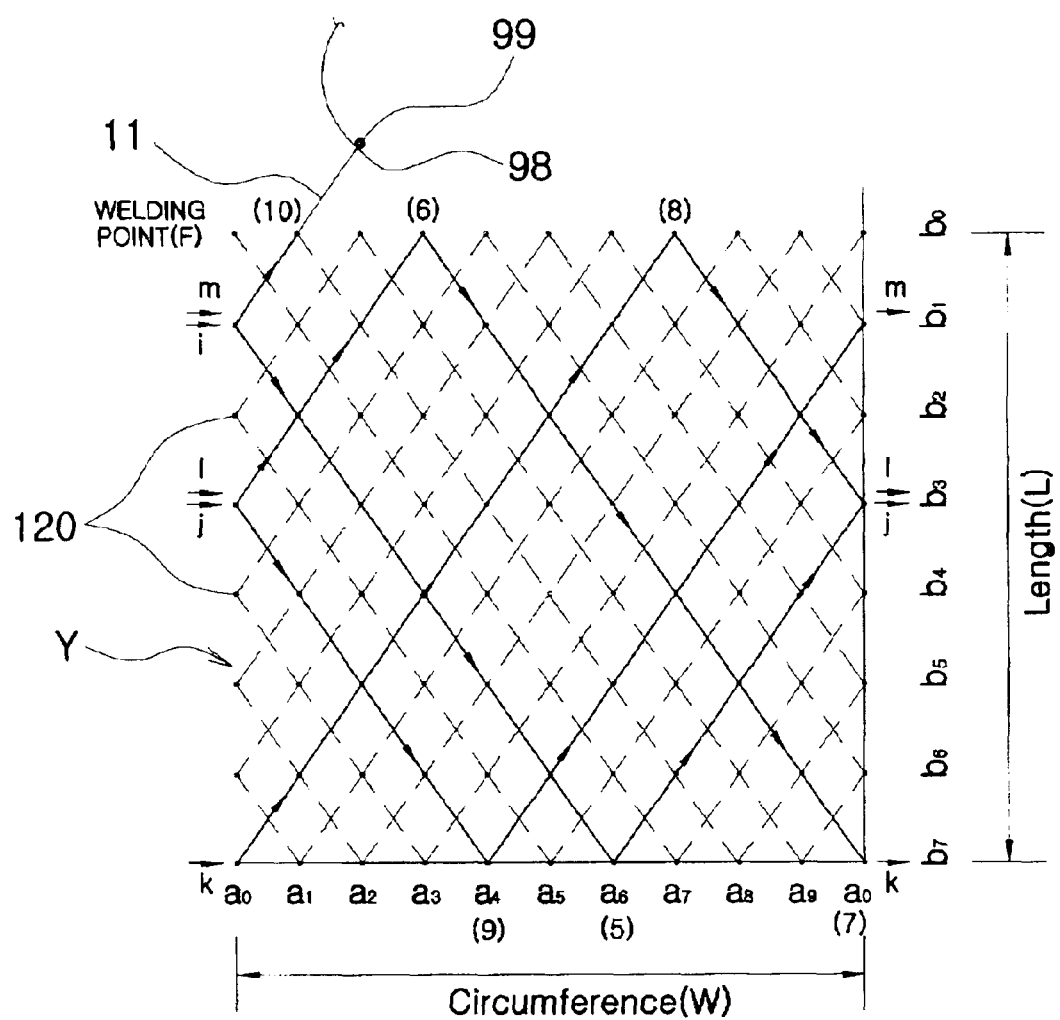

After the first cylindrical stent member X is fabricated, the second cylindrical stent member Y is fabricated. The fabrication of the second cylindrical stent member Y is illustrated in FIGS. 7c and 7d.

The second cylindrical stent member Y is fabricated while being passed by the projected pins 120 that are not utilized in fabricating the first cylindrical stent member X.

A knot 98 is formed by tying a second wire 11 at its one end. The knot 98 is inserted into a fixing pin 99 to secure the wire 10, which is indicated as a start point S.

In such a state, the second wire 11 is diagonally extended in parallel with the first wire 10 while being hooked around the projected pin (its position: a1b0), and is hooked around the projected pin (its position: a8b7) by passing the second wire 11 under the projected pin (its position: a8b7) situated in the lowest position ((1) position).

In such a case, if the second wire 11 firstly meets the previously positioned first wire 10 and is passed under the first wire 10 while being extended to the projected pin (its position: a8b7), the second wire 11 has to be passed over the previously positioned first wire 10 that is secondly met by the second wire 11. The second wire 11 is alternately passed under and over the first wire 10 in such a way.

The second wire 11 is hooked by passing the second wire 11 under the projected pin (its position: a8b5), and, thereafter, the second wire 11 is hooked around the uppermost projected pin 120 (its position: a0b5) by extending the second wire 11 to the uppermost projected pin 120 (its position: a5b0) and passing the second wire 11 under the uppermost projected pin 120 (its position: a5b0) (although in FIG. 7c the second wire 11 seems to be hooked around the projected pin 120 (its position: a0b5), the second wire 11 is extended along arrow "g") ((2) position).

In such a state, the second wire 11 is bent by extending the second wire 11 under the projected pin 120 (its position: a2b7) ((3) position).

In this case, although in FIG. 7c the second wire 11 seems to be hooked around the projected pin 120 (its position: a0b5), the second wire 11 is actually extended along arrow "h" because FIG. 7c is a development view.

In this state, the second wire 11 is bent by extending the second wire 11 over the projected pin 120 (its position: a9b0) ((4) position).

In this state, the second wire 11 is bent by extending the second wire 11 under the projected pin 120 (its position: a6b7) ((5) position).

In this case, although in FIG. 7c the second wire 11 seems to be hooked around the projected pin 120 (its position: a0b1), the second wire 11 is extended along arrow "i" of FIG. 7c and arrow "i" of FIG. 7d because FIG. 7c is a development view.

In this state, the second wire 11 is bent by extending the second wire 11 over the projected pin 120 (its position: a3b0) ((6) position).

In this case, although in FIG. 7d the second wire 11 seems to be hooked around the projected pin 120 (its position: a0b1), the second wire 11 is extended along arrow "j" because FIG. 7d is a development view.

In this state, the second wire 11 is bent by extending the second wire 11 over the projected pin 120 (its position: a0b7) ((7) position).

In this state (in FIG. 7d the movement of the second wire 11 is illustrated by arrow "k"), the second wire 11 is bent by extending the second wire 11 over the projected pin 120 (its position: a7b0) ((8) position).

In this state, the second wire 11 is bent by extending the second wire 11 under the projected pin 120 (its position: a4b7) ((9) position).

S In this case, although in FIG. 7d the second wire 11 seems to be hooked around the projected pin 120 (its position: a0b3), the second wire 11 is extended along arrow "1" because FIG. 7d is a development view.

In this state, the second wire 120 reaches the initial projected pin 120 (its position: a1b0) ((10) position).

There is fabricated the second cylindrical stent member Y in which its both ends are connected to each other by welding together both ends of the second wire 10 meeting each other, or inserting both ends of the first wire 10 into a thin, sleeve 200 and pressing them.

In this case, although in FIG. 7d the second wire 11 seems to be hooked around the projected pin 120 (its position: a0b1), the second wire 11 is extended along arrow "m" because FIG. 7d is a development view.

As described above, the second wire 11 is diagonally extended in parallel with the previously positioned first wire 10 and passed alternately under and over the first wire 10 so as to divide each of a plurality of rhombic spaces formed in the first cylindrical stent member X into four equal parts, thus forming the second cylindrical stent member Y. The second cylindrical stent member Y together with the first cylindrical stent member X functions to prevent the first and second cylindrical stent members X and Y from being separated from each other.

Additionally, the second cylindrical stent member Y utilizes the projected pins 120 other than the projected pins 120 that have been utilized by the first cylindrical stent member X.

As described above, the fabricating method of the present invention is performed while following a series of steps.

The first wire 10 undergoes the first step of being passed through the start point S, being bent by being extended by the diagonal length of 1 and being passed by a first projected pin 120, being bent by being diagonally downwardly extended by the diagonal length of 1 and passed under a second projected pin 120, being bent by being diagonally upwardly extended by the diagonal length of 1 and passed over a third projected pin 120, and being bent by being diagonally downwardly extended by the diagonal length of 2 and passed under a fourth projected pin 120.

The first wire 10 undergoes the second step of being bent by being diagonally upwardly extended by the diagonal length of and being passed over a fifth projected pin 120, being bent by being diagonally downwardly extended by the diagonal length of 1 and being passed under a sixth projected pin 120, being bent by being diagonally upwardly extended by the diagonal length of 1 and passed over a second projected pin 120, being bent by being diagonally downwardly extended by the diagonal length of 2 and passed under a seventh projected pin 120, and being bent by being diagonally upwardly extended by the diagonal length of 1 and passed over an eighth projected pin 120.

The first wire 10 undergoes the third step of being extended downwardly and upwardly six times each by a diagonal length of 1.

The first wire 10 undergoes the fourth step of following the first step, the second step, the first step, the second step, the first step, the second step, the third step, the reversed first step, the reversed second step, the reversed first step, the reversed second step and the reversed first step, and, thereafter, being extended downwardly and upwardly four times each by a diagonal length of 1.

The second wire 11 undergoes the first step, the second step five times, the fifth step of being extended downwardly and upwardly each by a diagonal length of 1, the reversed second step six times, and the reversed fourth step.

Figure 8:
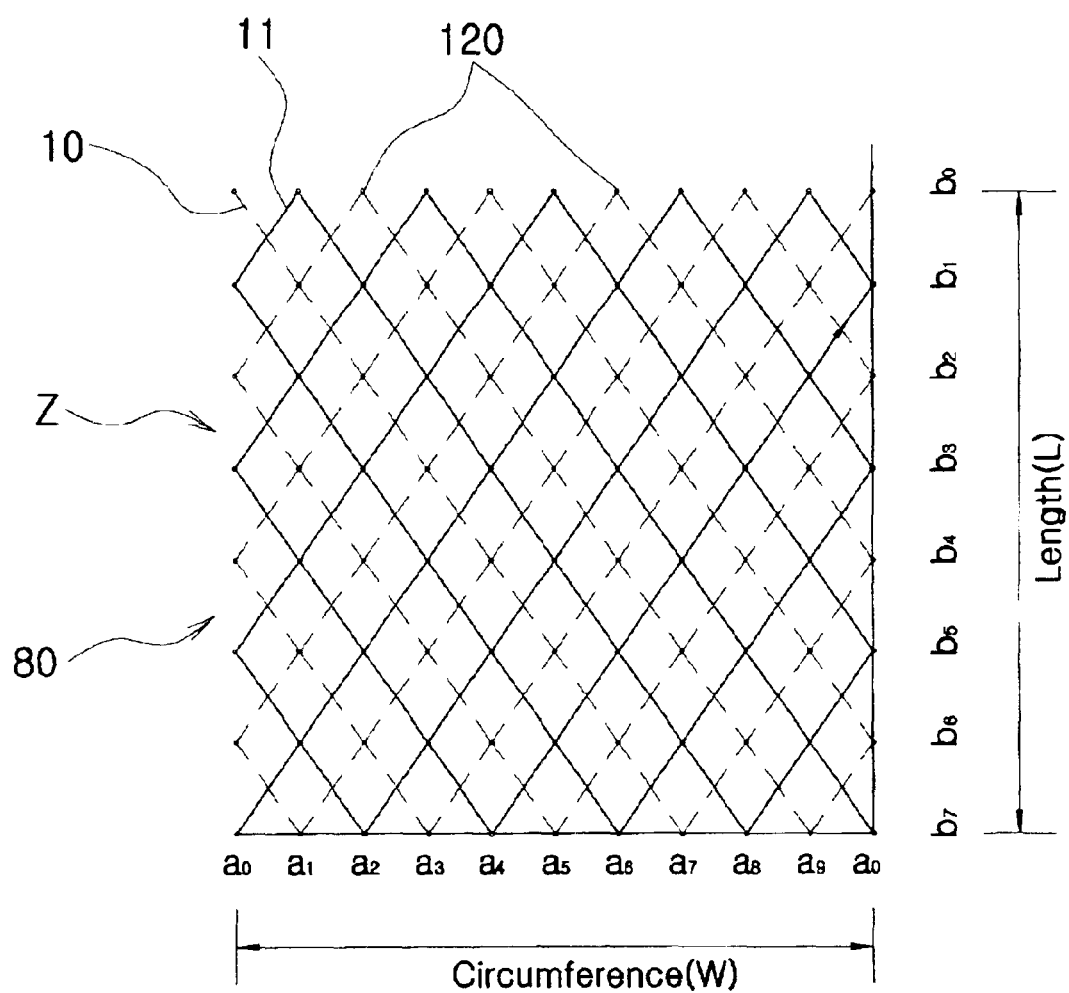
FIG. 8 is a development view showing a completed self-expandable stent.
Figure 9:
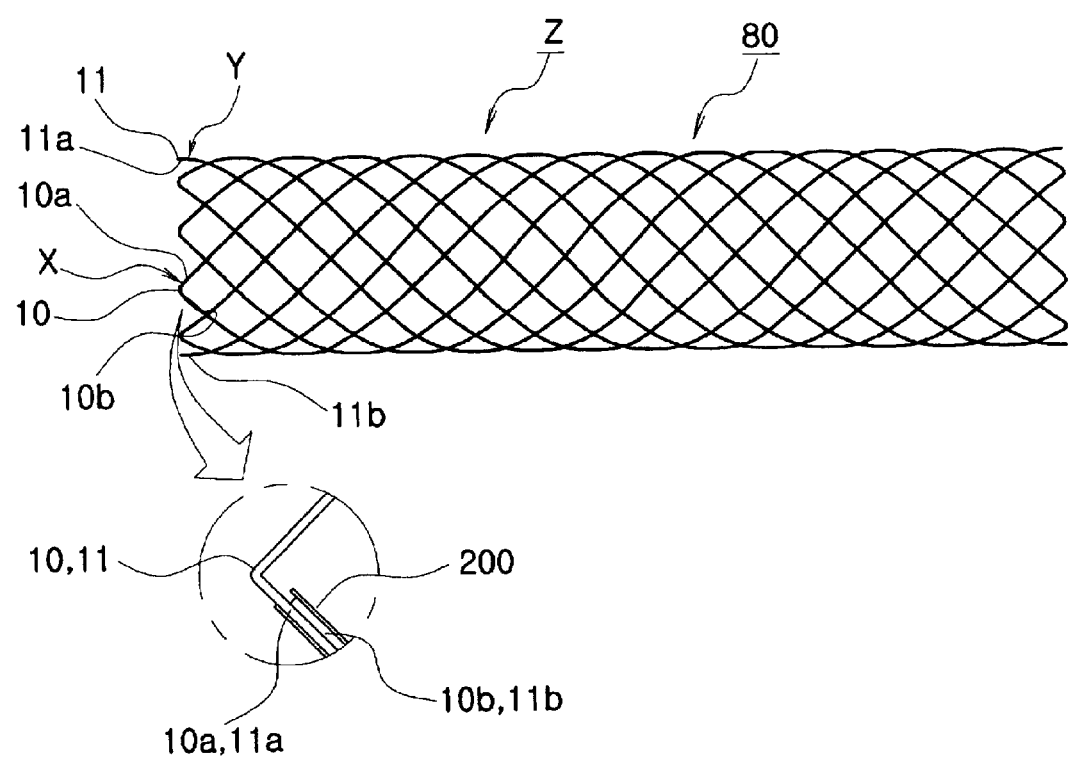
FIG. 9 is a front view showing the self-expandable stent of the present invention.
Figure 10:
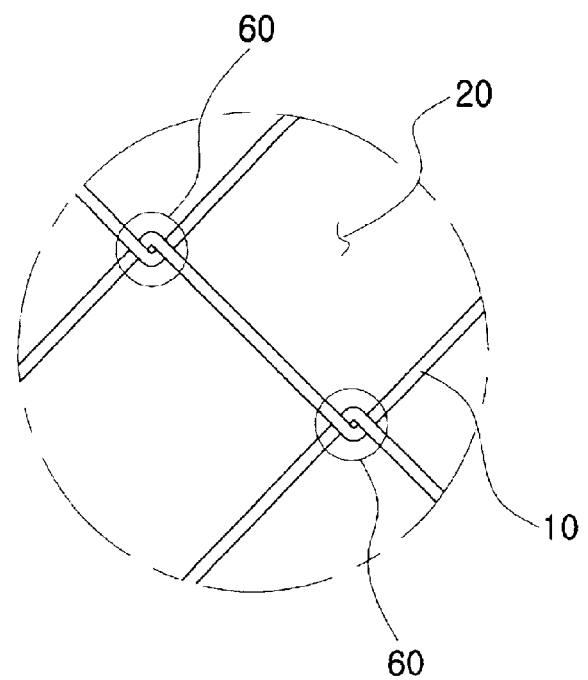
FIGS. 10 and 11 are detailed views showing the principal portions of the self-expandable stent of the present invention.
Figure 11:
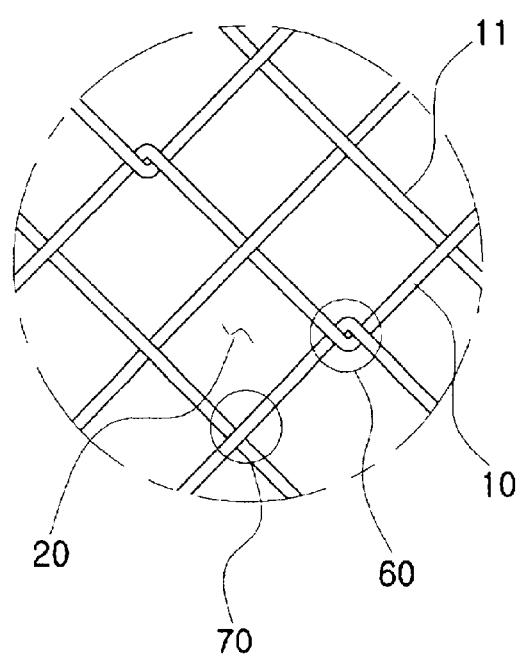
Figure 12:
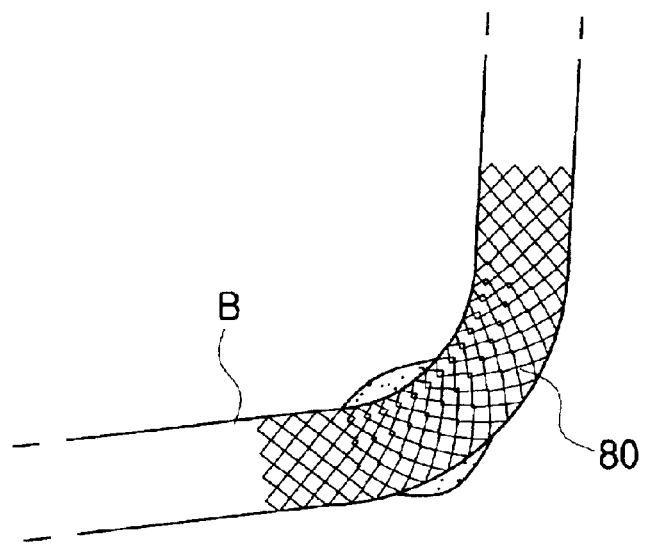
FIGS. 12 and 13 are views showing the application of the self-expandable stent of the present invention.
Figure 13:
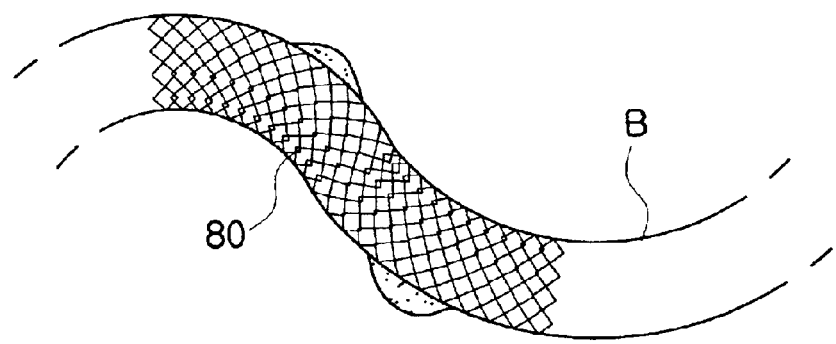

The hollow cylindrical body Z fabricated by performing the above-described steps is illustrated in FIG. 8 in the form of a development view. FIGS. 9 to 11 are a front view and detailed views of the fabricated hollow cylindrical body Z, respectively.

As shown in the drawings, the first wire 10 of super elastic shape memory alloy constituting the first cylindrical stent member X is bent a large number of times while being extended upwardly and downwardly a large number of times, so the first wire 10 forms a plurality of variable rhombic spaces 20 by forming a plurality of intersections 70 for causing the first wire 10 to be intersected with itself to resist the longitudinal constriction of the first cylindrical stent member X and a plurality of interlocked points 60 for causing the first wire 10 to be interlocked with itself at spaced positions to allow the longitudinal constriction of the first cylindrical stent member X.

The second wire 11 constituting the second cylindrical stent member Y is diagonally extended in parallel with the previously positioned first wire 10 and passed alternately under and over the first wire 10 so as to divide each of a plurality of rhombic spaces formed by the first cylindrical stent member X into four equal parts. Hence, the first and second cylindrical stent members X and Y are prevented from being separated from each other.

After the above-described fabrication steps, the first and second wires 10 and 11 are each welded together at both ends 10a and 10b, or 11a and 11b, and connected at both ends 10a and 10b, or 11a and 11b to each other by inserting the ends into the sleeve 200 and pressing them.

The self-expandable stent 80 is completed by cutting the remaining portion of both ends of each of the first and second wires 10 and 11, removing the projected pins 120 from the base jig 100, separating the hollow cylindrical body Z of the present invention from the base jig 100 and having the hollow cylindrical body z memorize its original shape through a heat treatment process.

In the present invention, the heat treatment process is completed in such a way that after the fabrication of the hollow cylindrical body Z, the hollow cylindrical body Z is allowed to memorize its original shape at the temperatures at which the hollow cylindrical body Z does not lose its elasticity.

The heat treatment, as disclosed in the previously filed patent application of the present inventor, is preferably performed at a temperature ranging from 350 to 600° C. for 8 to 30 minutes.

The super-elastic shape memory alloy wire is employed in the present invention. In the case of a super-elastic shape memory alloy wire having a diameter smaller than 0.1 mm, the self-elasticity of the super-elastic shape memory alloy wire is very low, so a stenosal portion cannot be sufficiently expanded by the fabricated self-expandable stent and the super-elastic shape memory alloy wire is not reliable; while in the case of a super-elastic shape memory alloy wire having a diameter greater than 0.5 mm, the hollow cylindrical body Z does not have sufficient rhombic spaces 20, so the hollow cylindrical body Z cannot be sufficiently reduced in volume. Hence, the super-elastic shape memory alloy has preferably a diameter of 0.1 to 0.5 mm.

Additionally, the number of the bends formed on each of both ends of the hollow cylindrical body Z is preferably less than 12. The reason for this is that a large number of the bends reduce the areas of rhombic spaces 20 regardless of the diameter of the super-elastic shape memory alloy wire, so the hollow cylindrical body Z cannot be sufficiently reduced in volume when in use.

However, when the number of the bends is less than three, the hollow cylindrical body Z can be sufficiently reduced, but the self-expandable stent 80 has a low elasticity even though the self-expandable stent 80 is restored to its memorized original shape. Consequently, the number of the bends is preferably three or more.

In the present invention, the first cylindrical stent member X is comprised of a plurality of rhombic spaces 20. As a result, when the first cylindrical stent member X is bent by external force, the rhombic spaces 20 situated on the inside of the first cylindrical stent member X bent are constricted whereas the rhombic spaces 20 situated on the outside of the first cylindrical stent member X bent are expanded. Therefore, when the first cylindrical stent member X is bent by external force, the first cylindrical stent member X can keep its bent shape (refer to FIGS. 12 and 13).

The first cylindrical stent member X is comprised of a plurality of rhombic spaces 20, so the rhombic spaces 20 are longitudinally compressed when longitudinal compression force is given to the first cylindrical stent member X, thereby causing the shortcoming that the entire length of the first cylindrical stent member X is shortened.

The shortcoming can be prevented by the second cylindrical stent member Y.

In more detail, the second cylindrical stent member Y undergoes the fabrication procedure that the second wire 11 are bent at its turning points while diagonally traversing the length L of the first cylindrical stent member X from one end to the other end. As a result, the first cylindrical stent member X interlocked with the second cylindrical stent member Y can maintain its original entire length L.

Therefore, the present invention overcomes the shortcoming of the invention simultaneously filed in Korea in which the self-expandable stent is longitudinally constricted.

As set forth beforehand, in this embodiment, the present invention is described using the circumference dividing lines a0, a1, a2, a3, - - - , a9 and the length dividing lines b0, b1, b2, b3, - - - , b7 set by regularly dividing the circumference W and length L of the of the cylinder 110 of the base jig 100, which is for easy understanding of the present invention. Accordingly, the circumference dividing lines and the length dividing lines can be optionally set according to the size of the stent 80, that is, the diameter and length of the stent 80.

A plurality of assembly grooves 130 are formed with reference to the circumference dividing lines a0, a1, a2, a3, - - - , a9, and the length dividing lines b0, b1, b2, b3, - - - , b7 can be set as described beforehand. The base jig 100 can be fabricated using the assembly grooves 130 and the setting.

Accordingly, expandable stents that are each fabricated of two wires and can be deformed to have a straight line or winding shape pertains to the scope of the present invention.

The expandable stent of the present invention is utilized in the same way as that for the method of the patent application previously filed by the present inventors.

However, in the self-expandable stent 80 of the present invention, the rhombic spaces 20 defined by the interlocked points 60 and intersections 70 of the first cylindrical stent member X can be varied by external force. Accordingly, the self-expandable stent 80 can be deformed in its bend such as a blood vessel or the gall duct and varied in diameter Ø, so the self-expandable stent 80 can expand the stenosal portions within the gullet, the gall duct or the urethra while maintaining the original shape of the stenosal portion.

In particular, the interlocked points 60 are comprised of the spaced bends of the wires 10 and 11, so the self-expandable stent 80 does not damage the inner wall of the blood vessel B when inserted and removed.

As described above, the present invention provides a self-expandable stent used to be situated in and expand the passage of a stenosal portion, which is capable of being positioned to fit the shape of the passage of the stenosal portion regardless of the shape of the passage, such as a straight (horizontal or vertical) passage and a winding passage, while maintaining its transversal elasticity, thereby expanding the passage of the stenosal portion to its original shape.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A self-expandable stent using shape memory alloy, comprising:

a first cylindrical stent member comprised of a first wire formed of super elastic shape memory alloy, said first wire being bent a large number of times while being extended upwardly and downwardly a large number of times, so said first wire forms a plurality of variable rhombic spaces by forming a plurality of intersections for causing said first wire to be intersected with itself to resist longitudinal constriction of said first cylindrical stent member and a plurality of interlocked points for causing said first wire to be interlocked with itself at spaced positions to allow longitudinal constriction of said first cylindrical stent member; and a second cylindrical stent member comprised of a second wire formed of super elastic shape memory alloy, said second wire being diagonally extended in parallel with the previously positioned first wire and passed alternately under and over the first wire so as to divide each of a plurality of rhombic spaces formed in the first cylindrical stent member into four equal parts, thereby preventing said first and second cylindrical stent members from being separated from each other.

* * * * *